United States Patent [19]
Wright, Jr.

[11] 3,968,230

[45] July 6, 1976

[54] COMPOSITIONS CONTAINING BENZODIAZEPINDIONES AND METHOD OF USE

[75] Inventor: William Blythe Wright, Jr., Woodcliff Lake, N.J.

[73] Assignee: American Cyanamid Company, Stamford, Conn.

[22] Filed: June 16, 1975

[21] Appl. No.: 587,012

Related U.S. Application Data

[63] Continuation-in-part of Ser. No. 464,424, April 26, 1974, abandoned.

[52] U.S. Cl. .................................................. 424/274
[51] Int. Cl.² ............................................... A61K 31/40
[58] Field of Search ................................... 424/274

Primary Examiner—Stanley J. Friedman
Attorney, Agent, or Firm—Denis A. Polyn

[57] ABSTRACT

Compositions containing 1,2,3,11a-tetrahydro-10-methyl-5H-pyrrolo[2,1-c][1,4]benzodiazepin-5,11(10H)-dione in the form of its dextrorotatory isomer and as a racemic mixture and method of use are described. The active component in its different forms is useful in treating anxiety in warm-blooded animals.

3 Claims, No Drawings

COMPOSITIONS CONTAINING BENZODIAZEPINDIONES AND METHOD OF USE

This application is a continuation-in-part of my application Ser. No. 464,424, filed Apr. 26, 1974 now abandoned.

DESCRIPTION OF THE INVENTION

This invention relates to new compositions and method of use in its dextrorotatory or racemic form of 1,2,3,11a-tetrahydro-10-methyl-5H-pyrrolo[2,1-c][1,4]benzodiazepin-5,11(10H)-dione.

The active component of the novel compositions of the present invention may be illustrated by the following formula:

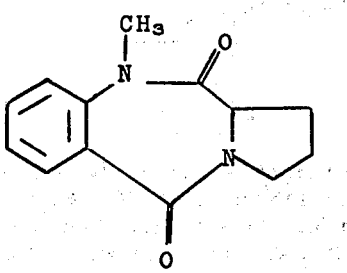

This compound is a solid at room temperature, soluble in methanol, ethanol, benzene, acetone and ethyl acetate, but having limited solubility in hexane and water, the dextrorotatory isomer having an optical rotation $[\alpha]_D^{25}$ of +486° at a concentration of 1% in methanol and a melting point of 120°–122°C.

The compounds of this invention may be prepared by the following method which has been found most desirable.

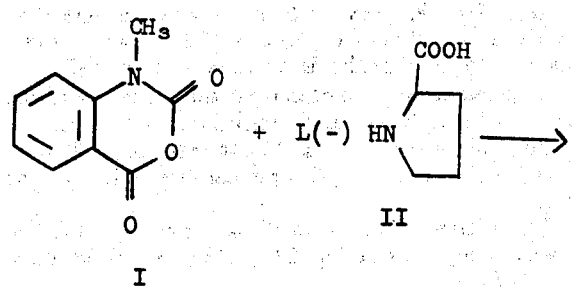

N-Methyl isatoic anhydride (I) and L-proline (II) are reacted in a solvent such as ethanol or dimethyl sulfoxide at 25° to 200°C. for a period of 1 to 24 hours to produce the dextrorotatory isomer of 1,2,3,11a-tetrahydro-10-methyl-5H-pyrrolo[2,1-c] [1,4]benzodiazepin-5,11(10H)-dione.

Alternatively, the dextrorotatory isomer may be prepared by the following two-step process involving the reaction of L(−)-proline and N-methyl isatoic anhydride to produce the intermediate L(−)-1-(N-methylanthraniloy)proline:

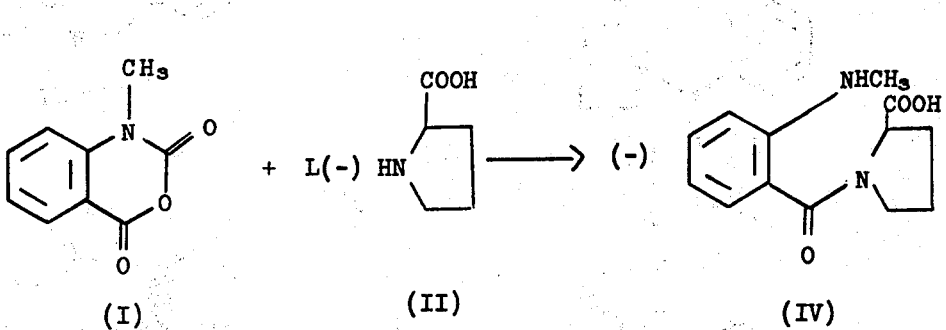

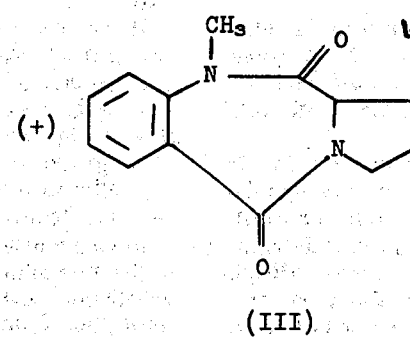

N-Methyl isatoic anhydride (I) and L-proline (II) are reacted in dimethyl sulfoxide for 20 to 120 minutes at 50° to 100°C. to produce L(−)-1-(N-methylanthraniloyl)proline (IV), which is recovered and then heated in an oil bath at 145°C. to 200°C. for 10 to 60 minutes to produce the dextrorotatory isomer (III).

Cyclization may also be carried out by contacting the L(−)-1-(N-methylanthraniloyl)proline (IV) with a condensing agent such as thionyl chloride, N,N'-carbonyldiimidazole, dicyclohexylcarbodiimide or the like.

The racemic (DL) form of this compound may be prepared by substituting DL-proline in any of these reactions.

As an alternative to the second method, the same starting material may be reacted in dimethylsulfoxide at 25° to 200°C. for 1 to 24 hours to produce the subject dextrorotatory isomer.

In still another method, N-methylisatoic anhydride (I) is first reacted with an ester of proline (V) to form an intermediate 1-(N-methylanthraniloyl)proline ester (VI) which is then cyclized to III by heating, by heating under acidic or alkaline conditions or by reacting in the presence of an amide forming reagent.

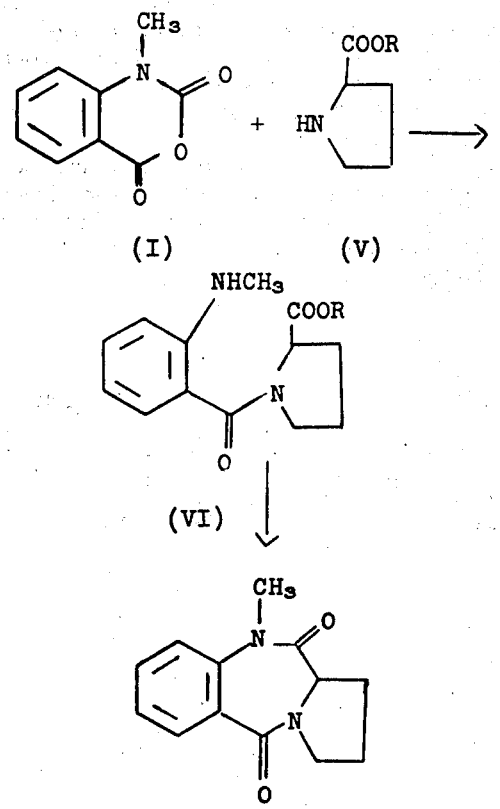

wherein R is hydrogen, alkyl $C_1$-$C_{10}$, or benzyl and the like. Alternatively, other agents such as N-methylanthranilic acid, acid chloride, esters or anhydride may be similarly condensed with proline or proline ester and cyclized.

The active component can also be prepared by the alkylation of the analogous desmethyl compound in the presence of an alkali catalyst. For example, a mixture of 1,2,3,11a-tetrahydro-5H-pyrrolo[2]-benzodiazepin-5,11(10H)-dione (VIII), sodium methoxide, ethanol and methyliodide is allowed to react at room temperature for 24 hours and the desired compound (III) is then removed.

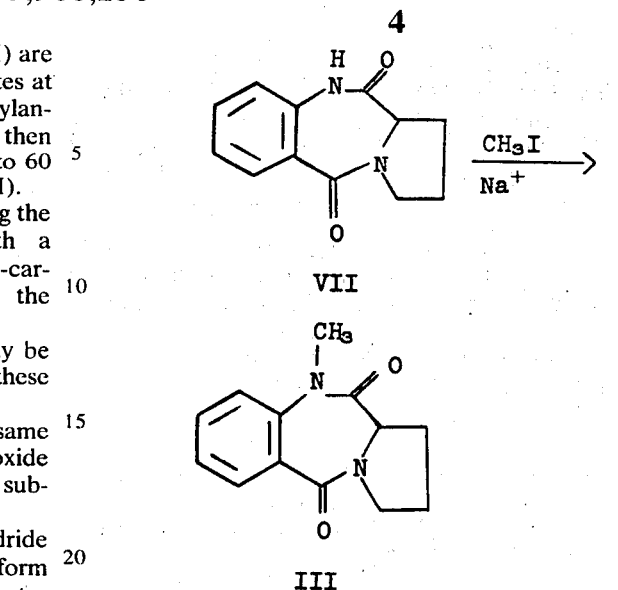

The following method can also be used to prepare the compounds of this invention (III) by the cyclization of N-(pyrrolidine-2-carbonyl)anthranilic acid or its esters (VIII) by heating with or without an alkaline catalyst such as sodium methylate at a temperature of about 150°–210°C. or by treating with an amide forming cyclizing agent such as thionyl chloride, N,N'-carbonyldiimidazole, or dicyclohexylcarbodiimide.

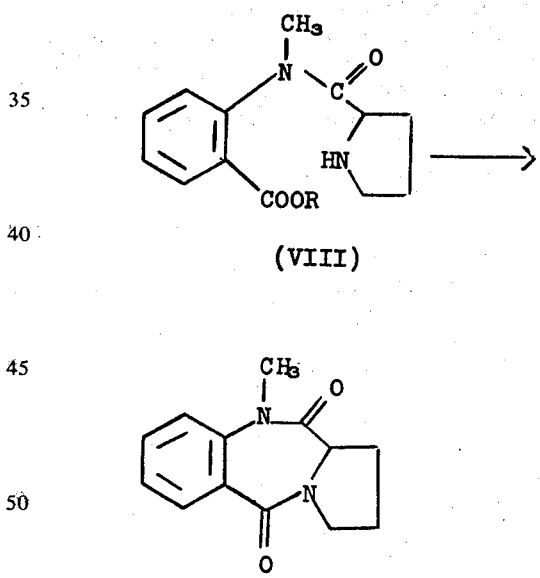

where R is hydrogen, alkyl $C_1$-$C_{10}$ or benzyl and the like.

The active components of the present invention possess central nervous system activity at non-toxic doses, and as such, are useful as anxiolytic agents. The compounds have been tested pharmacologically and found to have the above properties which show a desirable wide spread between doses producing anxiolytic activity and toxic symptoms. Depressant properties are absent at effective anxiolytic doses.

The anti-anxiety properties of the active components of the present invention have been established in a test which indicates anxiolytic activity by a measure of protection from convulsions resulting from the administration of pentylenetetrazol. Graded dose levels of the dextro and racemic forms of the compound 1,2,3,11a-tetrahydro-10-mthyl-5H-pyrrolo[2,1-c] [1,4]benzodiazepin-5,11(10H)-dione are administered orally, in a 2% starch vehicle, to groups of at least 5 rats. At the estimated time of peak effect, the rats are treated intravenously with pentylenetetrazole at a dose of 21 to 23 mg./kg. of body weight. This dose is estimated to cause clonic seizures in 99% of unprotected rats. The effective dose of the test compound for protection of 50% of the animals is calculated by the method of J. T. Litchfield and F. Wilcoxon, Journal of Pharmacology and Experimental Therapeutics, 96, 99 (1949). The results are given in the table which follows in comparison with Librium (chlordiazepoxide), Valium (diazepam) and the dextro and racemic forms of 1,2,3,11a-tetrahydro-5H-pyrrolo[2,1-c] [1,4]benzodiazepin-5,11(10H)-dione (U.S. Pat. No. 3,732,212) all of which were tested in exactly the same manner. It has been reported [R. T. Hill and D. R. Tedeschi, "Animal Testing and Screening Procedures in Evaluating Psychotropic Drugs" in An Introduction to Psychopharmacology, Eds. R. R. Rech and K. E. Moore, Raven Press, New York, pp. 237–288 (1971) that there is a high degree of correlation between antagonism of pentylenetetrazole seizures in rats and antianxiety effects in higher warm-blooded animals.

Parenteral solutions and suspensions may be prepared for intramuscular or subcutaneous administration, and suppositories may be prepared for rectal administration. Such compositions and preparations should contain at least 0.1% of active component. The percentage of the compositions and preparations may, of course, be varied, and may conveniently be between 2 to 60% or more of the weight of the unit. The amount of active component in such therapeutically useful compositions or preparations is such that a suitable dosage of from about 1.0 to about 10.0 mg/kg/day for the dextrorotatory isomer and from about 2.0 to about 25.0 mg/kg/day for the racemic mixture will be obtained. Preferred compositions or preparations according to the present invention are prepared so that a dosage unit form contains between about 20 and about 300 mg. of the therapeutically active component.

The compositions of this invention are physiologically active as anxiolytic agents. As such, they can be incorporated in various pharmaceutical forms such as set forth immediately above, for immediate or sustained release, by conbining with suitable pharmaceutical carriers They may be in the form of dosage units for a single therapeutic dose or in small units for multiple dosages or in larger units for division into single doses. Obviously, in addition to the therapeutic tranquilizing

TABLE

Protection Against Clonic Seizures Caused by Pentylenetetrazole In Rats

| Compound | Median Effective Oral Dose (mg/kg) $ED_{50}$ |
|---|---|
| 1. Dextro-1,2,3,11a-tetrahydro-10-methyl-5H-pyrrolo[2,1-c][1,4]benzodiazepin-5,11(10H)-dione | 10 |
| 2. Racemic-1,2,3,11a-tetrahydro-10-methyl-5H-pyrrolo[2,1-c][1,4]benzodiazepin-5,11(10H)-dione | 20 |
| 3. Dextro-1,2,3,11a-tetrahydro-5H-pyrrolo[2,1-c]-[1,4]-benzodiazepin-5,11(10H)-dione | 35 |
| 4. Racemic-1,2,3,11a-tetrahydro-5H-pyrrolo[2,1-c]-[1,4]benzodiazepin-5,11(10H)-dione | 70 |
| 5. Librium (chlordiazepoxide) | 2.5 |
| 6. Valium (diazepam) | 1.8 |

It can be seen from the above results that the dextrorotatory and racemic forms of 1,2,3,11a-tetrahydro-10-methyl-5H-pyrrolo[2,1-c] [1,4]benzodiazepin-5,11(10H)-dione (Compounds 1 and 2) are far more effective as anxiolytic agents than the respective dextrorotatory and racemic forms of the closest prior art compound 1,2,3,11a-tetrahydro-5H-pyrrolo[2,1-c] [1,4]benzodiazepin-5,11(10H)-dione (Compounds 3 and 4).

The active components of the present invention may be administered to warm-blooded animals, in either its dextrorotatory or racemic forms, orally, or parenterally if desired, and when so administered, may be considered as a tranquilizing agent for therapeutically desired treatment of anxiety in warm-blooded animals. The dosage regimen can be adjusted to provide optimum therapeutic response. Thus, for example, several doses may be administered daily, or the dose may be reduced proportionately as indicated by the requirements of the particular therapeutic situation.

For therapeutic administration the active compound of this invention may be incorporated with pharmaceutical carriers such as excipients and used, for example, in the form of tablets, dragees, capsules, liquids, elixirs, emulsions, suspensions, syrups, chocolate, candy, wafers, chewing gum or the like for oral administration.

compound there may be present excipients, binders, fillers and other therapeutically inert ingredients necessary in the formulation of the desired pharmaceutical preparation.

SPECIFIC DISCLOSURE

The following specific examples illustrate the preparation of the compounds of the present invention along with formulations of the active component. Parts are by weight unless otherwise indicated.

EXAMPLE 1

Preparation of Dextrorotatory 1,2,3,11a-Tetrahydro-10-methyl-5H-pyrrolo[2,1-c] [1,4]benzodiazepin-5,11(10H)-dione 1

A mixture of 17.7 g. of N-methyl isatoic anhydride, 11.5 g. of L-proline and 250 ml. of ethanol is heated on a steam bath for 3 hours and then concentrated to remove the ethanol. The residue is mixed with benzene and a small portion of water and the layers are separated. The benzene layer is washed twice with water and concentrated to remove the solvent. The residue is triturated with ether. The crystals which form are collected by filtration and recrystallized from ethyl acetate yielding the pure dextrorotatory isomer, melting point 120°–122°C., $[\alpha]_D^{25}$ +486°(1%, methanol).

EXAMPLE 2

Preparation of Racemic (DL)
1,2,3,11a-Tetrahydro-10-methyl-5H-pyrrolo[2,1-c]
[1,4]benzodiazepin-5,11(10)-dione The racemic compound is obtained by substituting DL-proline in place of L-proline in the procedure of Example 1. The racemate melts at 124°–126°C.

EXAMPLE 3

Preparation of Dextrorotatory
1,2,3,11a-Tetrahydro-10-methyl-5H-pyrrolo[2,1-c]
[1,4]benzodiazepin-5,11(10H)-dione A mixture of 12.3 g. of L-proline, 17.7 g. of N-mthyl isatoic anhydride and 100 ml. of dimethyl sulfoxide is heated on a steam bath for 40 minutes. The mixture is cooled and diluted with 250 ml. of cold water. The precipitate is recovered by filtration, washed with water and then ether, air dried and then recrystallized from ethanol yielding the intermediate L-1-(N-methylanthrailoyl)proline, melting point 140°–142°C., $[\alpha]_D^{25}$ −165°C. (1.1%, methanol).

This intermediate is placed in a round bottom flask and immersed in an oil bath heated to 170°–180°C. for 30 minutes. The material is dissolved in ethyl acetate and cooled. The desired dextrorotatory product separates as crystals which are recovered by filtration.

EXAMPLE 4

Preparation of Dextrorotatory
1,2,3,11a-Tetrahydro-10-methyl-5H-pyrrolo[2,1-c]
[1,4]benzodiazepin-5,11(10H)-dione A mixture of 12.3 g. of L-proline, 17.7 g. of N-methyl isatoic anhydride and 100 ml. of dimethyl sulfoxide is heated on a steam bath for 6 hours, cooled and then dilted with 250 ml. of water. The reaction mixture is extracted three times with benzene. The combined benzene layers are washed with water and concentrated to remove the solvent. The residue is recrystallized from ethyl acetate yielding the pure dextrorotatory isomer.

EXAMPLE 5

The present compounds can be dispensed in dosage unit forms such as hard shell capsules or soft shell capsules. A formulation found useful in the preparation of such capsules is as follows:

| | Grams | Grams |
|---|---|---|
| Dextro-1,2,3,11a-tetrahydro-10-methyl-5H-pyrrolo[2,1-c][1,4]-benzodiazepin-5,11(10H)-dione | 25 | — |
| Racemic-1,2,3,11a-tetrahydro-10-methyl-5H-pyrrolo[2,1-c]-[1,4]benzodiazepin-5,11(10H)-dione | — | 50 |
| Lactose U.S.P. | 3,000 | 3,000 |
| Magnesium stearate (0.5%) | 31.25 | 31.25 |
| | 3,056.25 | 3,081.25 |

The formulation is thoroughly mixed and placed as equal quantities in 1000 capsules. Each capsule of either formulation represents about 25 mg. of active component.

EXAMPLE 6

The following example represents a formulation useful in preparing tablets. These tablets can be prepared with sufficient active ingredient for a portion of one days use. Larger tablets can be scored and divided into halves or quantities to be given one to four times per day. Obviously, smaller tablets can be used in multiple doses to obtain the daily dose.

| | Per Tablet | |
|---|---|---|
| Dextro-1,2,3,11a-tetrahydro-10-methyl-5H-pyrrolo-[2,1-c][1,4]-benzodiazepin-5,11(10H)-dione | 50 mg. | — |
| Racemic-1,2,3,11a-tetrahydro-10-methyl-5H-pyrrolo-[2,1-c]-[1,4]benzodiazepin-5,11(10H)-dione | — | 100 mg. |
| Corn Starch | 420 mg. | 420 mg. |
| Methylcellulose 400 | 700 mg. | 700 mg. |
| Magnesium stearate (1%) | 364 mg. | 364 mg. |
| | 1,534 mg. | 1,584 mg. |

Each tablet contains 50 mg. of the dextro or 100 mg. of the racemic form of the active component.

EXAMPLE 7

The active component of the present invention can also be given in the form of tablets made by other formulations such as:

| | Per Tablet | |
|---|---|---|
| Dextro-1,2,3,11a-tetrahydro-10-methyl-5H-pyrrolo-[2,1-c][1,4]-benzodiazepin-5,11(10H)-dione | 25 mg. | — |
| Racemic-1,2,3,11a-tetrahydro-10-methyl-5H-pyrrolo[2,1-c][1,4]-benzodiazepin-5,11(10H)-dione | — | 50 mg. |
| Corn Starch | 300 mg. | 300 mg. |
| Ethyl cellulose | 5 mg. | 5 mg. |
| Magnesium stearate | 1.6 mg. | 1.6 mg. |
| | 331.6 mg. | 356.6 mg. |

The above formulation can be varied by increasing or decreasing the corn starch and by the addition of other ingredients. Also, other disintegrating agents, such as potato starch, may be used in place of corn starch. Other lubricants such as stearic acid, talc and the like can be used. Sweetening agents such as saccharin or sodium cyclohexyl sulfamate and flavoring such as peppermint oil, oil of wintergreen, orange or cherry can be used.

EXAMPLE 8

Preparation of Racemic
1,2,3,11a-Tetrahydro-10-methyl-5H-pyrrolo[2,1-c]
[1,4]benzodiazepin-5,11(10H)-dione A mixture of 4.32 g. of 1,2,3,11a-tetrahydro-5H-pyrrolo[2,1-c] [1,4]benzodiazepin-5,11(10H)-dione, 1.2 g. of sodium methylate and 40 ml. of ethanol is stirred at room temperature for 3 hours and 3 ml. of methyl iodide is added. The reaction mixture is stirred for 6 hours longer and concentrated. The residue is mixed with benzene and water and the layers are separated. The benzene layer is washed with water and concentrated. The product is further purified by recrystallization from ethyl acetate and melts at 124°–126°C.

EXAMPLE 9

Preparation of Dextrorotatory
1,2,3,11a-Tetrahydro-10-methyl-5H-pyrrolo[2,1-cl]
[1,4]benzodiazepin-5,11(10H)-dione A mixture of 24.8 g. of (−)-1-(N-methylanthraniloyl)proline and 300 ml. of benzene is stirred and 12.0 g. of thionyl chloride is added dropwise. The mixture is heated at relux temperature for 2 hours, cooled, washed twice with water and concentrated to recover the (+)-1,2,3,11a-tetrahydro-10-methyl-5H-pyrrolo[2,1c] [1,4]benzodiazepin-5,11(10H)dione.

EXAMPLE 10

Preparation of Dextrorotatory 1,2,3,11a-Tetrahydro-10-methyl-5H-pyrrolo[2,1-c][1,4]benzodiazepin-5,11(10H)-dione A mixture of 24.8 g. of (−)-1-(N-methylanthraniloyl)proline and 18.0 g. of N,N'-carbonyldiimidazole in 300 ml. of dry tetrahydrofuran is stirred for 2 hours at room temperature and then heated at reflux temperature for 3 hours. The reaction mixture is concentrated to remove the solvent and the residue is extracted into benzene. The benzene solution is washed twice with water and concentrated to recover the desired product.

EXAMPLE 11

Preparation of Racemic 1,2,3,11a-Tetrahydro-10-methyl-5H-pyrrolo[2,1-c][1,4]benzodiazepin-5,11(10H)-dione A mixture of 24.8 g. of racemic 1-(N-methylanthraniloyl)proline and 21 g. of dicyclohexylcarbonyl diimide in 300 ml. of tetrahydrofuran is stirred at room temperature for 24 hours and then heated on the steam bath for 4 hours. The reaction mixture is filtered to remove the insoluble dicyclohexyl urea and the mother liquid is concentrated to recover the desired product, which is further purified by recrystallization from ethyl acetate.

EXAMPLE 12

Preparation of Racemic 1,2,3,11a-Tetrahydro-10-methyl-5H-pyrrolo[2,1-c][1,4]benzodiazepin-5,11(10H)-dione A mixture of 17.7 g. of N-methylisatoic anhydride, 15.0 g. of the ethyl ester of proline and 100 ml. of dimethylsulfoxide is heated on a steam bath for 40 minutes. The mixture is cooled and diluted with 250 ml. of cold water. The reaction mixture is extracted with benzene and the benzene solution is concentrated to recover the ethyl ester of 1-(N-methylanthraniloyl)-proline.

Ten grams of the above ester is dissolved in 150 ml. of 2N ethanolic hydrochloric acid and heated at reflux temperature for 8 hours. The reaction mixture is concentrated to remove the solvent and the residue is purified by liquid chromatography using hexane/methanol and a celite column.

The embodiments of the invention in which an exclusive property or privilege is claimed are defined as follows:

1. A method of treating anxiety in a warm-blooded animal which comprises administering internally to said warm-blooded animal an anti-anxiety amount of 1,2,3,11a-tetrahydro-10-methyl-5H-pyrrolo[2,1-c][1,4]benzodiazepin-5,11(10 H)-dione and a pharmaceutically acceptable carrier therefor.

2. A method according to claim 1, in which the active component is the dextrorotatory isomer of 1,2,3,11a-tetrahydro-10-methyl-5H-pyrrolo[2,1-c][1,4-benzodiazepin-5,11(10H)-dione.

3. The process according to claim 1, in which the active component is the racemic mixture of 1,2,3,11a-tetrahydro-10-methyl-5H-pyrrolo[2,1-c][1,4]benzodiazepin-5,11(10H)dione isomers.

* * * * *